United States Patent
Kraft et al.

(10) Patent No.: US 9,131,308 B2
(45) Date of Patent: Sep. 8, 2015

(54) PASSIVE AUDIO EAR FILTERS WITH MULTIPLE FILTER ELEMENTS

(71) Applicant: Doppler Labs, Inc., New York, NY (US)

(72) Inventors: Noah Kraft, Brooklyn, NY (US); Richard Fritz Lanman, New York, NY (US); Dan Wiggins, Montecito, CA (US); Jonathan Oswaks, Thousand Oaks, CA (US); Nils Jacob Palmborg, Brooklyn, NY (US)

(73) Assignee: Dopler Labs, Inc., New York, NY (US)

( * ) Notice: Subject to any disclaimer, the term of this patent is extended or adjusted under 35 U.S.C. 154(b) by 0 days.

(21) Appl. No.: 14/601,901

(22) Filed: Jan. 21, 2015

(65) Prior Publication Data

US 2015/0208170 A1    Jul. 23, 2015

Related U.S. Application Data

(60) Provisional application No. 61/929,788, filed on Jan. 21, 2014.

(51) Int. Cl.
*H04R 3/04*    (2006.01)
*A61F 11/08*   (2006.01)

(52) U.S. Cl.
CPC ............. *H04R 3/04* (2013.01); *A61F 2011/085* (2013.01)

(58) Field of Classification Search
CPC ... A61F 11/06; A61F 11/08; A61F 2011/085; A61F 11/10
USPC .................................. 181/135; 128/867, 868
See application file for complete search history.

(56) References Cited

U.S. PATENT DOCUMENTS

| | | | | |
|---|---|---|---|---|
| 4,852,683 | A * | 8/1989 | Killion ........................ | 181/130 |
| 5,113,967 | A * | 5/1992 | Killion et al. ................ | 181/132 |
| 7,740,104 | B1 * | 6/2010 | Parkins et al. ............... | 181/135 |
| 8,186,478 | B1 * | 5/2012 | Grason ........................ | 181/175 |
| 2006/0042865 | A1 * | 3/2006 | Berg et al. .................... | 181/135 |
| 2006/0045284 | A1 * | 3/2006 | Haussmann et al. .......... | 381/72 |
| 2007/0125590 | A1 * | 6/2007 | Oberdanner .................. | 181/135 |
| 2010/0294285 | A1 * | 11/2010 | Turdjian ...................... | 128/867 |
| 2011/0235843 | A1 * | 9/2011 | Keady et al. ................. | 381/380 |
| 2012/0305329 | A1 * | 12/2012 | Keady et al. ................. | 181/135 |
| 2014/0146989 | A1 * | 5/2014 | Goldstein ..................... | 381/380 |
| 2014/0190494 | A1 * | 7/2014 | Ely .............................. | 128/868 |
| 2015/0043743 | A1 * | 2/2015 | Meegan et al. ............... | 381/72 |

\* cited by examiner

*Primary Examiner* — Jeremy Luks
(74) *Attorney, Agent, or Firm* — SoCal IP Law Group LLP; John E. Gunther; Steven C. Sereboff

(57) ABSTRACT

There is disclosed a passive acoustical filter including two or more filter elements coupled between an ambient and a listener's ear, each of the filter elements selected from the group consisting of a low pass filter element, a high pass filter element, a band reject filter element, and a band pass filter element.

12 Claims, 18 Drawing Sheets

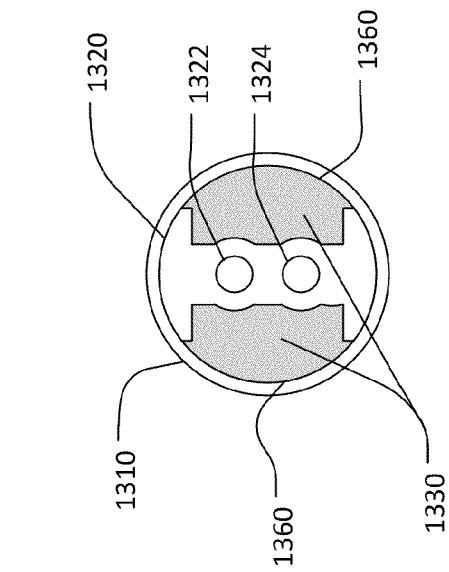
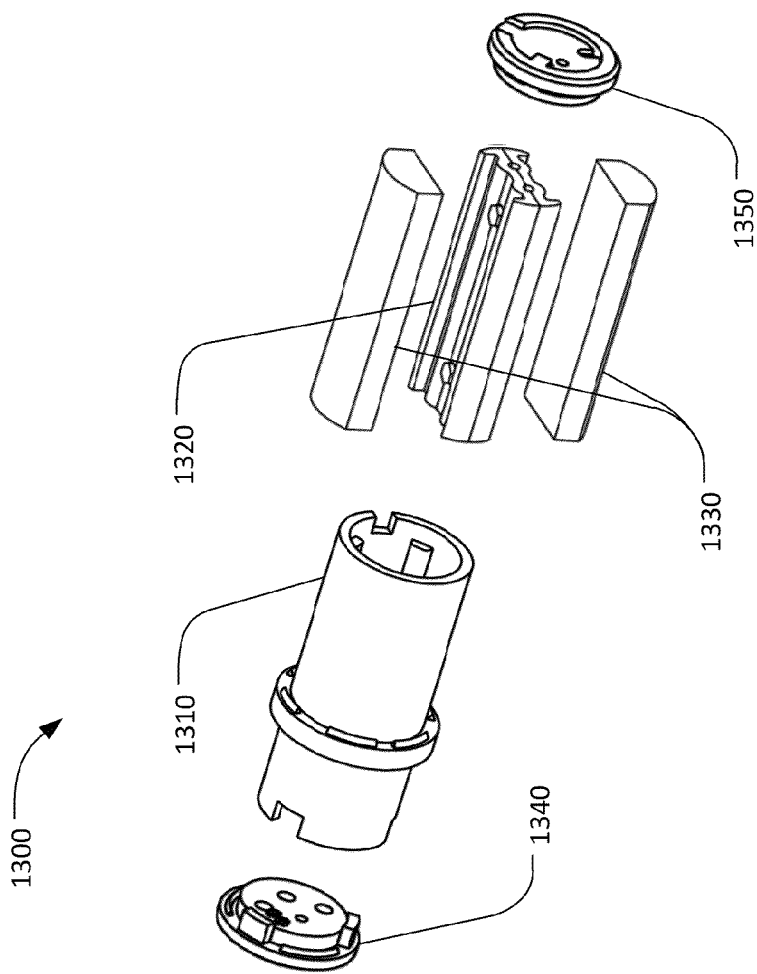
FIG. 13B
FIG. 13A

PASSIVE AUDIO EAR FILTERS WITH MULTIPLE FILTER ELEMENTS

RELATED APPLICATION INFORMATION

This patent claims priority from the Provisional Patent Application No. 61/929,788, entitled PASSIVE AUDIO EAR FILTERS, filed Jan. 21, 2014.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

1. Field

This disclosure relates generally to passive audio ear filters that can attenuate certain sound frequencies and allow other frequencies to pass through unchanged.

2. Description of the Related Art

Exposure to sound at certain sound pressure levels and sound frequencies can, over time, cause hearing loss.

Humans' perception to sound varies with both frequency and sound pressure level (SPL). For example, humans do not perceive low and high frequency sounds as well as they perceive midrange frequencies sounds (e.g., 500 Hz to 6,000 Hz). Further, human hearing is more responsive to sound at high frequencies compared to low frequencies. FIG. 1 illustrates equal loudness contours defined in ISO (International Standards Organization) Standard 226(2003). The X axis represents sound frequency measured in Hertz (Hz) and the Y axis represents sound pressure level measured in decibels (dB) relative to a pressure level of $2 \times 10^{-5}$ Pascal. The unit of measurement for loudness levels is the phon, and is arrived at by reference to equal-loudness contours. FIG. 1 shows equal loudness contours for loudness levels of 20, 40, 60, 80, and 100 phon. Each equal-loudness contour defines the sound pressure level, over the frequency spectrum, for which a listener perceives a constant loudness when presented with pure steady tones. FIG. 1 also shows the hearing threshold level.

Hearing protection that attenuates sound equally at all frequencies, or otherwise without regard to the variation of hearing sensitivity with frequency, may attenuate potentially damaging sounds at the expense of pleasurable sounds. For example, an ear filter providing uniform attenuation of 20 dB would reduce loudness by about 20 phon at 1 kHz and 40 phon at 20 Hz. Thus the relative loudness of low frequency sounds would be substantially reduced relative to the loudness of higher frequency sounds. However, with attention to the hearing response curves, it is possible to design ear filters that attenuate damaging sound levels and maintain, or even enhance, desired sounds.

There are many situations where people desire protection from sounds at certain frequencies, while allowing sounds at other frequencies to reach their ears. For example, at a concert, concert goers might want to enjoy the music, but also be protected from the mid-range and high levels of sound frequencies that cause damage to a person's hearing. On an airplane, passengers might wish to block out the roar of the engine, but not conversation. At a sports event, fans might desire to hear the action of the game, but receive protection from the roar of the crowd. While sleeping, people might want protection from all auditory disturbances. These are just a few common examples where people wish to hear some, but not all, of the sound frequencies in their environment.

DESCRIPTION OF THE DRAWINGS

FIG. 13A is a graphical image of components of a representative music acoustical filter.

FIG. 13B is a schematic cross-sectional view of a music acoustical filter assembled form the components shown in FIG. 13A.

DETAILED DESCRIPTION

Passive acoustical filters incorporating multiple filter elements can protect the ear from damaging sound frequencies while allowing less damaging sound frequencies to reach the ear. In this document, the term "filter element" refers to an acoustic filter that provides a single filter function such as a low-pass, high-pass, band-pass, or band-reject filter function. The term "passive acoustical filter" refers to a filter device that includes one or more filter element coupled between an ambient and a listener's ear. Two or more filter elements are considered to be "coupled between the ambient and the listener's ear" if ambient sound must pass through at least one of the filter elements before reaching the listener's ear. Two or more filter elements are considered to be "in series" if ambient sound must pass consecutively through all of the two or more filter elements before reaching the listener's ear. Two or more filter elements are considered to be "in parallel" if the filter elements provide alternate paths for ambient sound to reach the listener's ear. Unless otherwise stated, ambient sound may be divided approximately equally between parallel filter elements. The term "earbud" means an apparatus configured to fit, at least partially, within and be supported by a user's ear. Typically, a portion of an earbud fits against or within the user's outer ear canal. Other portions of an earbud may fit within the concha or pinna of the user's ear.

Such passive acoustical filters can be designed compactly in order to fit within an earbud, headphone, or other apparatus that can be placed into or outside an ear. Further, such passive acoustical filters can be designed to attenuate certain damaging and/or disturbing sound frequencies associated with specific environments and/or activities. For example, a passive acoustical filter may include a series of low-pass filter elements in parallel with a high-pass filter element and can attenuate damaging mid-range frequencies associated with attending a concert. For further example, a passive acoustical filter may provide a low-pass filter element and a high-pass filter element in parallel, and can attenuate mid-range frequencies associated with attending a sports event or participating in motor sport activities. Yet another exemplary passive acoustical filter may include a series of low-pass filter elements, and can attenuate mid and high-range frequencies associated with sounds disturbing to sleep. Other passive acoustical filters are possible that provide different types of filter elements alone, in parallel, in series, and/or in parallel/series combinations to attenuate unwanted frequencies associated with specific activities and/or environments, while allowing desired frequencies to pass through.

Figure 2:
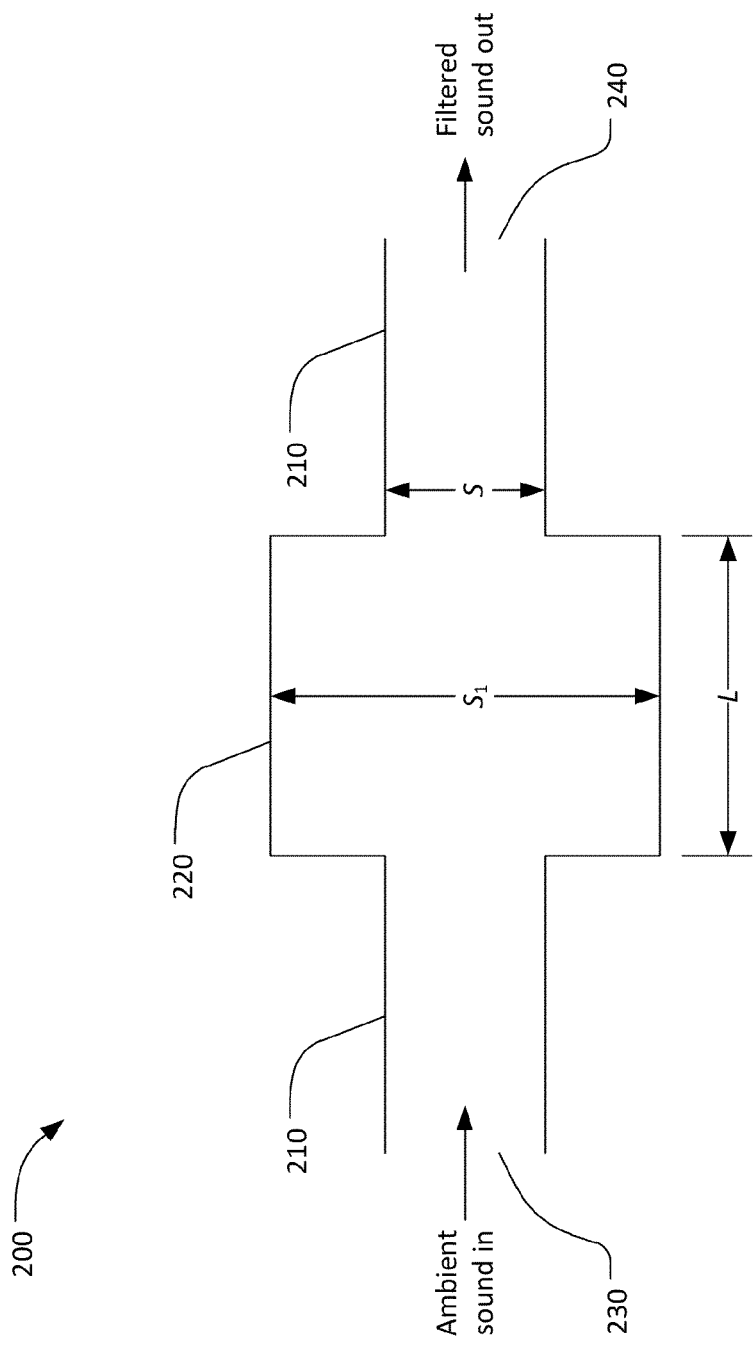
FIG. 2 is a schematic cross-sectional view of an exemplary low-pass filter element.

FIG. 2 is a schematic cross-sectional view of an exemplary low-pass filter element. The low-pass filter element 200 includes a main branch 210 and a single expansion chamber 220. In operation, ambient sound can enter an opening 230 of the low-pass filter 200, and certain sound frequencies can be filtered as the ambient sound passes through the main branch 210 and expansion chamber 220. The resulting filtered sound can exit the opening 240 at the opposite end of the low-pass filter element 200.

The following equation can be used to calculate the dimensions needed for a low-pass filter element to achieve a desired cutoff frequency (i.e., the frequency at which the filter starts to have effect):

$$f_c = \left(\frac{cS}{\pi L(S_1 - S)}\right)$$

Where:
$f_c$=the cutoff frequency of the filter;
c=speed of sound (343 m/s in air);
S=diameter of the main branch of the filter;
$S_1$=diameter of the expansion chamber of the low-pass filter; and
L=length of the expansion chamber of the low-pass filter.

Figure 3:
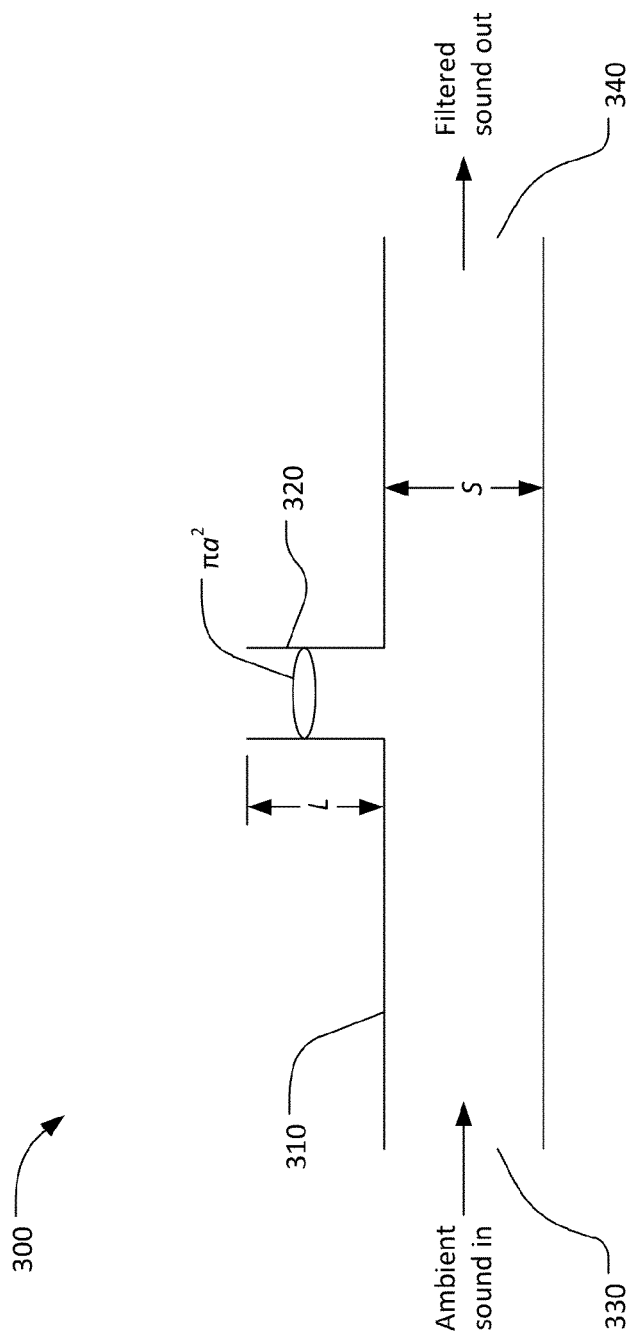
FIG. 3 is a schematic cross-sectional view of an exemplary high-pass filter element.

FIG. 3 is a schematic cross-sectional view of an exemplary high-pass filter element. The high-pass filter element 300 includes a main branch 310 and a side branch 320. In operation, ambient sound can enter an opening 330 of the high-pass filter element 300, and certain sound frequencies can be filtered as the ambient sound passes through the main branch 310 and side branch 320. The resulting filtered sound can exit the opening 340 at the opposite end of the high-pass filter element 300.

The following equation can be used to calculate the dimensions needed for a high-pass filter element to achieve a desired cutoff frequency:

$$f_c = \left(\frac{ca^2}{2SL}\right)$$

Where:
$f_c$=the cutoff frequency of the filter;
c=speed of sound (343 m/s in air);
S=diameter of the main branch of the filter;
L=the length of the side branch of the high-pass filter; and
a=radius of the side branch of the high-pass filter.

Figure 4:
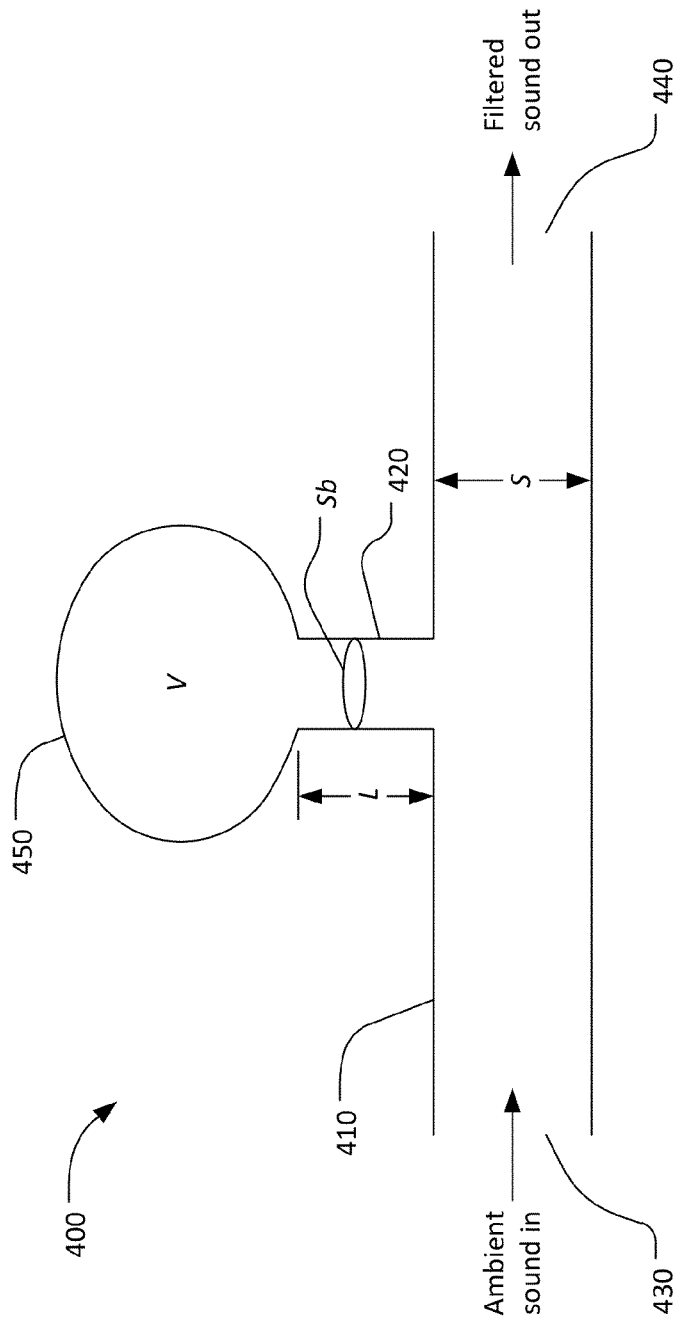
FIG. 4 is a schematic cross-sectional view of an exemplary band-reject filter element.

FIG. 4 is a schematic cross-sectional view of an exemplary band-reject filter element. The band-reject filter element 400 includes a main branch 410, a volume neck 420, and an expansion chamber 450. In operation, ambient sound can enter an opening 430 of the band-reject filter element 400, and certain sound frequencies can be filtered as the ambient sound passes through the main branch 410, volume neck 420 and expansion chamber 450. The resulting filtered sound can exit the opening 440 at the opposite end of the band-reject filter element 400.

The following equation can be used to calculate the dimensions needed for a band-reject filter element to achieve a desired cutoff frequency:

$$f_c = \left(\frac{c}{2\pi}\right)\sqrt{\left(\frac{S_b}{LV}\right)}$$

Where:
$f_c$=the cutoff frequency of the filter;
c=speed of sound (343 m/s in air);
L=the length of the volume neck for a band-reject filter;
$S_b$=area of the volume neck for a band-reject filter; and
V=volume of the expansion chamber for a band-reject filter.

The frequencies at which a filter element is effective are dictated by the shape and size of the filter element, as well as the medium within the filter element. The conduction of sound waves through a medium is dependent upon the ratio of the bulk modulus of the medium to the density of the medium, and is governed by the Newton-Laplace equation:

$$c = \sqrt{\frac{K}{\rho}}$$

Where:
c is the speed of sound;
K is the bulk modulus of the medium; and
ρ is the density of the medium.

In some embodiments, the filter element dimensions needed for a given frequency effect can be reduced by inserting a medium within the filter element that has a ratio of bulk modulus to density (K/ρ) less than air to slow down the speed of sound. For example, slowing the speed of sound by a factor of two can reduce the dimensions of the acoustical filter equally by a factor of two. In air, the speed of sound is approximately 343 meters per second (at 20° C., 1 atm). For example, a reticulated (i.e., open-cell structure) material that has a K/ρ ratio lower than air can be placed inside the acoustical filters to reduce the speed of sound, while still allowing passage of sound through the filter. Suitable materials may include polyurethane, polyester, polystyrene, or other plastic foam, and processed plastic and organic fibers like cotton, bamboo, and yarn.

As will be described below, a combination of acoustical filter elements can be used to achieve a target response curve for a particular environment and/or activities that protects the ear from certain damaging or disturbing sound frequencies while allowing other sound frequencies to reach the ear.

Figure 5:
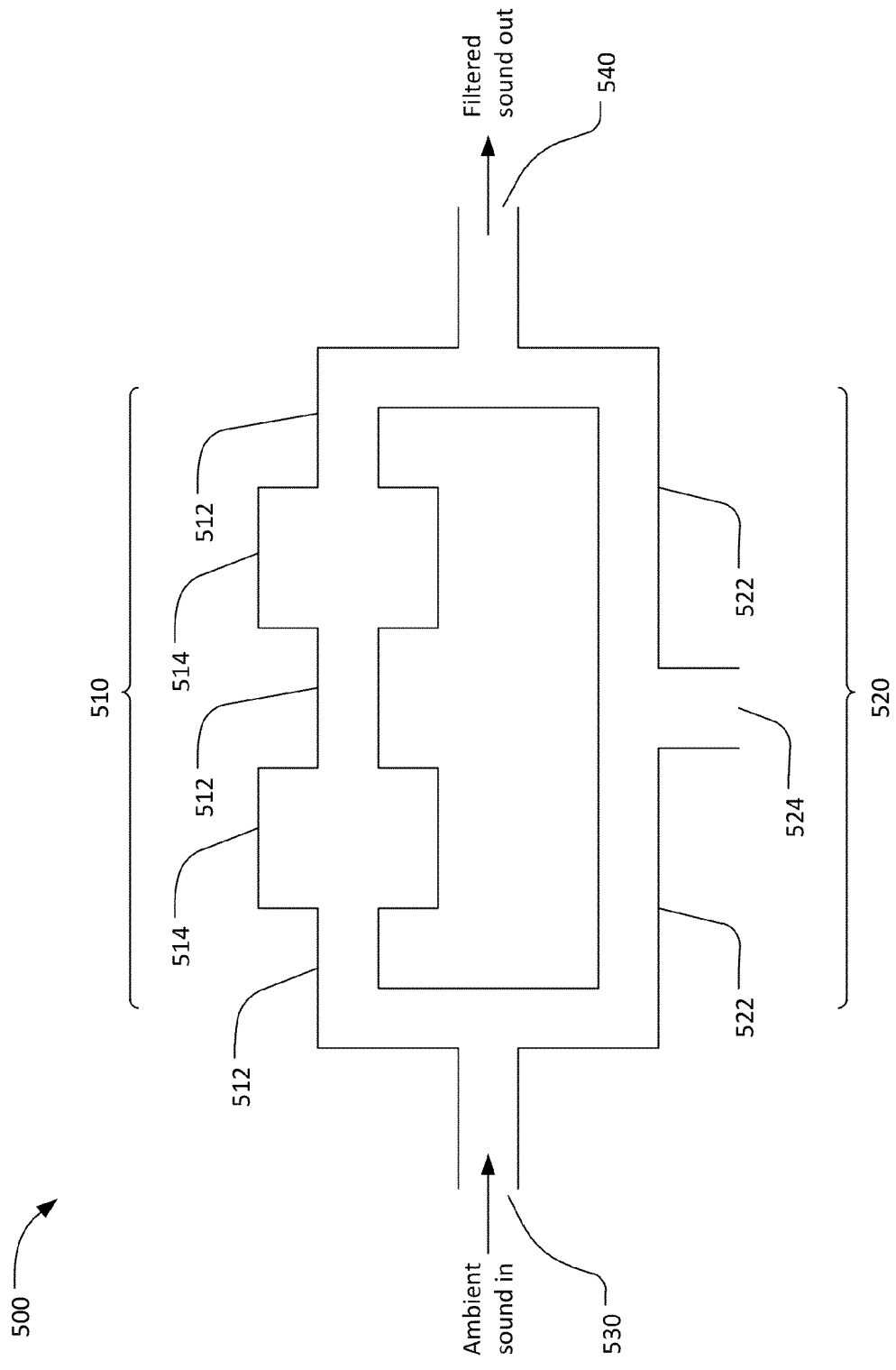
FIG. 5 is a schematic diagram of a passive acoustical filter including a series of low-pass filter elements in parallel with a high-pass filter element.

FIG. 5 is a schematic diagram of a passive acoustical filter 500 that can be used within an earbud, headphone or other apparatus to protect a human's auditory system from hearing damage and/or audio disturbance associated with attending musical events. The passive acoustical filter 500 includes a double-stage low-pass filter element 510 arranged in parallel with a single stage high-pass filter element 520. The configuration of a double-stage low-pass filter element in parallel with a single stage high-pass filter element will be referred to herein as a "music acoustical filter". The double-stage low-pass filter element 510 consists of two low-pass filter elements in series. The low-pass filter elements include respective expansion chambers 514 connected by a main branch 512. In operation, ambient sound can enter the passive acoustical filter 500 at one opening 530 and certain sound frequencies can be filtered as the ambient sound passes through the high-pass filter element 520 and the dual-stage low-pass filter element 510. The resulting filtered sound can exit the passive acoustic filter 500 at the opposite opening 540. The filtered sound exiting at 540 may be approximately the sum of the sound passing through the double-stage low-pass filter element 510 and the sound passing through the high-pass filter element 520.

Exemplary dimensions for the double stage low-pass filter element 510, are set forth in Table 1 below:

TABLE 1

| Exemplary dimensions for the double-stage low-pass filter element 505 | |
|---|---|
| Main branch 512 diameter | 0.5 mm |
| Expansion chamber 514 diameter | 2.6 mm |
| Expansion chamber 514 length | 14 mm |

These dimensions can be derived from the equation for the low-pass filter element set forth above. Further, these dimensions can be useful for creating a compact passive acoustic filter that can be inserted into ear buds, headphones or other apparatuses that fit into or outside an ear and for achieving an exemplary cutoff frequency for each low-pass filter of approximately 300 Hz. Unless otherwise stated, the term "approximately" means plus-or-minus 20%. In this example, the resonant frequencies of the two low-pass filter elements are the same. However, in other music filter designs, the resonant frequencies and dimensions of the two low-pass filter elements may differ.

Further, a reticulated material, for example a foam material having a density of 0.5 g/cm³ and bulk modulus 27 kPA, can be used in the music acoustical filter illustrated in FIG. 5 to reduce the speed of sound (e.g., to 200 m/s). The foam material or other reticulated material can optionally be placed in both expansion chambers 514 of the double stage low-pass filter 510 to reduce the speed of sound and to help keep the dimensions of the music acoustic filter compact. For the double-stage low-pass filter 510 having the dimensions disclosed in Table 1, filling the expansion chambers with foam of these parameters would lower the cutoff frequency from approximately 300 Hz to approximately 200 Hz.

Passive acoustical filter 500 also includes a high-pass filter element 520 having a main branch 522, and single side branch 524. Exemplary dimensions for the high-pass filter element 520, are set forth in Table 2 below:

TABLE 2

| Exemplary Dimensions for the high-pass filter element 520 | |
|---|---|
| Side branch 524 diameter | 0.5 mm |
| Side branch 524 length | 3.0 |
| Main branch 522 diameter | 0.55 mm |

These dimensions can be derived from the equation for the high-pass filter element set forth above. Further, these dimensions can be useful for creating a compact passive acoustic filter that can be inserted into ear buds, headphones or other apparatuses that fit into or outside an ear and for achieving an exemplary cutoff frequency of approximately 18,200 Hz.

The dimensions described above for the passive acoustical filter 500 are non-limiting examples, and other dimensions that can achieve similar hearing protection may also be used. Additionally, the dimensions described above can be tailored to attenuate frequencies associated with specific genres of music. Further, the frequency response of a music acoustical filter can be selected to suit the venue of a musical event. For example, the cut-off frequencies of the low-pass filter elements may be 50 to 3000 Hz, and the cutoff frequency of the high pass filter element may be 1,000 to 25,000 Hz.

Figure 1:
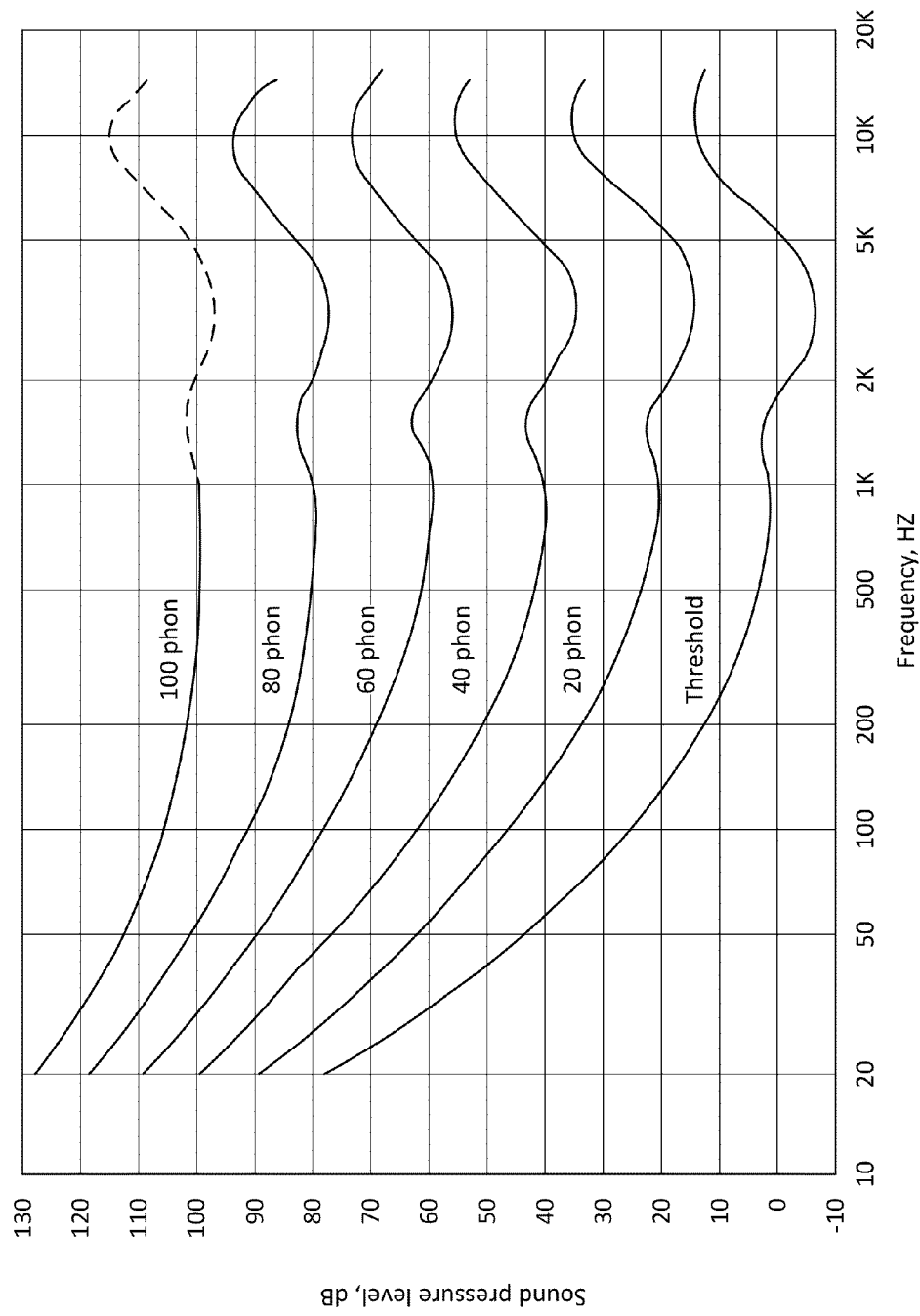
FIG. 1 is a graph of equal-loudness contours.
Figure 6:
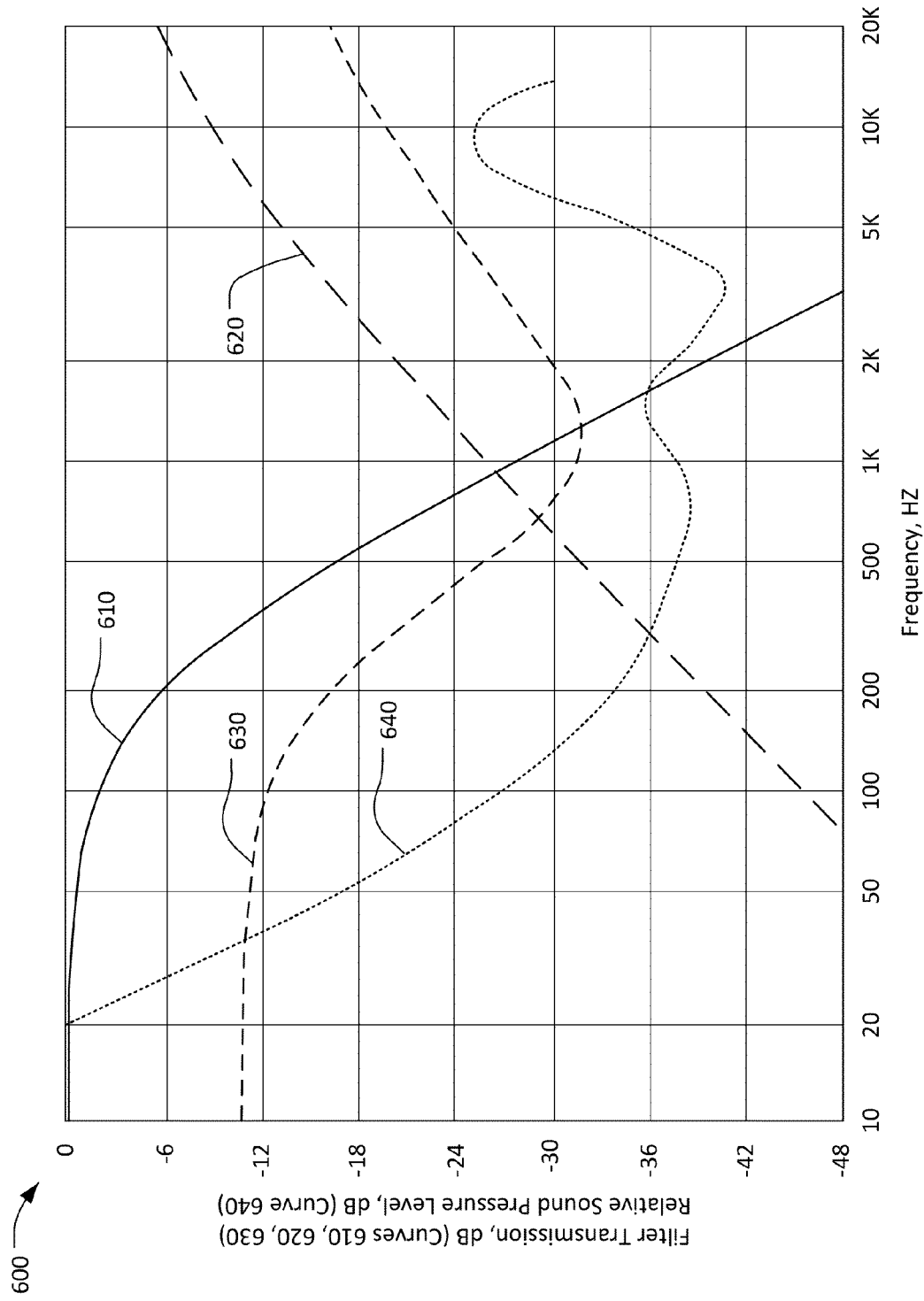
FIG. 6 is a graph of attenuation curves relating to the passive acoustical filter of FIG. 5.

FIG. 6 is a graph of transmission curves relating to a music acoustic filter having the general configuration of the passive acoustic filter 500 as shown in FIG. 5. The transmission curves are plotted along an X axis that represents sound frequency measured in hertz (Hz) and a Y axis that represents transmission (inverse of attenuation) of a passive acoustic filter or filter element measured in decibels (dB). The curve 610 represents the transmission of a loss-less double-stage low-pass filter element having the dimensions given in Table 1, including the incorporation of reticulated material in the expansion chambers of the double-stage low-pass filter elements. The curve 620 represents the transmission of a loss-less high-pass filter element having the dimensions given in Table 2. The curve 630 represents the combined transmission of the double stage low-pass filter in parallel with the single stage high-pass filter, including frequency independent attenuation that occurs in the small diameter main branches of the filter elements. The curve 640 is the 80 Phon loudness level from FIG. 1, normalized to 0 dB at 20 Hz. The curve 640 represents the sound pressure level required to produce apparently equal loudness as a function of frequency. As illustrated in FIG. 6, the performance of the passive acoustic filter (as summarized by the transmission curve 630) compliments the 80 Phon equal loudness curve 640, in that the filter provides highest attenuation (lowest transmission) at frequencies where the human ear is most sensitive, and lowest attenuation (highest transmission) for low and high frequencies where the ear is less sensitive.

Figure 7:
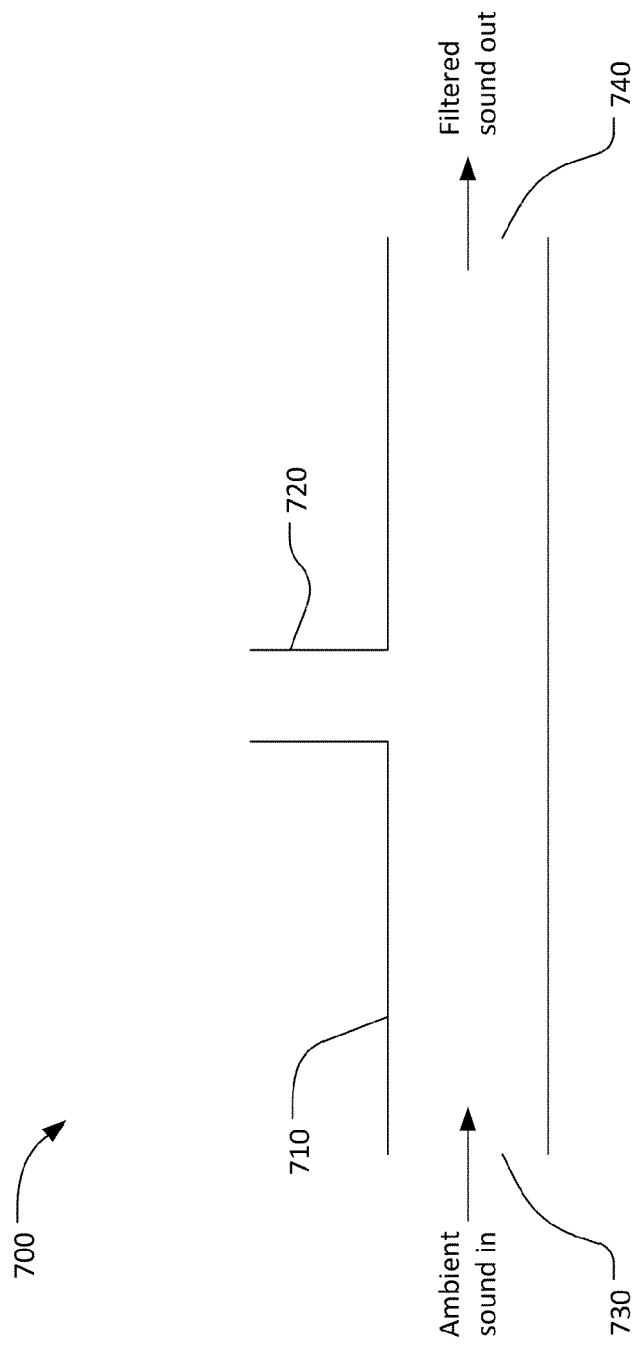
FIG. 7 is a schematic diagram of an exemplary high-pass filter element.

FIG. 7 is a schematic diagram of a passive acoustical filter 700 that can be used within an ear bud, headphone or other apparatus to protect a human's auditory system from hearing damage and/or audio disturbance associated with air and train travel. The passive acoustical filter 700 includes a single stage high-pass filter element having a main branch 710 and a side branch 720. The configuration of a single high-pass filter element will be referred to herein as a "travel acoustic filter".

In operation, ambient sound can enter the passive acoustical filter 700 at one opening 730, and certain sound frequencies can be filtered as the ambient sound passes through the main branch 710 and side branch 720. The resulting filtered sound can exit the passive acoustical filter 700 at the opposite opening 740.

Exemplary dimensions for the passive acoustical filter 700, in accordance with an embodiment of the disclosed subject matter, are set forth in Table 3 below:

TABLE 3

| Exemplary dimensions for the passive acoustical filter 700 | |
|---|---|
| Side branch 720 diameter | 2 mm |
| Side branch 710 length | 20 mm |
| Main branch 710 diameter | 2 mm |

The above disclosed dimensions can be derived from the equation for the high-pass filter element set forth above. Further, these dimensions can be useful for creating a compact filter that can be inserted into earbuds, headphones or other apparatuses that fit into or outside an ear, and for achieving an exemplary cutoff frequency of approximately 1850 Hz.

A reticulated material having dimensions approximate to the side branch 720 may optionally be placed into the side branch 720 to slow down the speed of sound and reduce the cutoff frequency to approximately 925 Hz.

The dimensions described above for the travel acoustical filter are non-limiting examples, and other dimensions that can achieve similar hearing protection may also be used.

Figure 8:
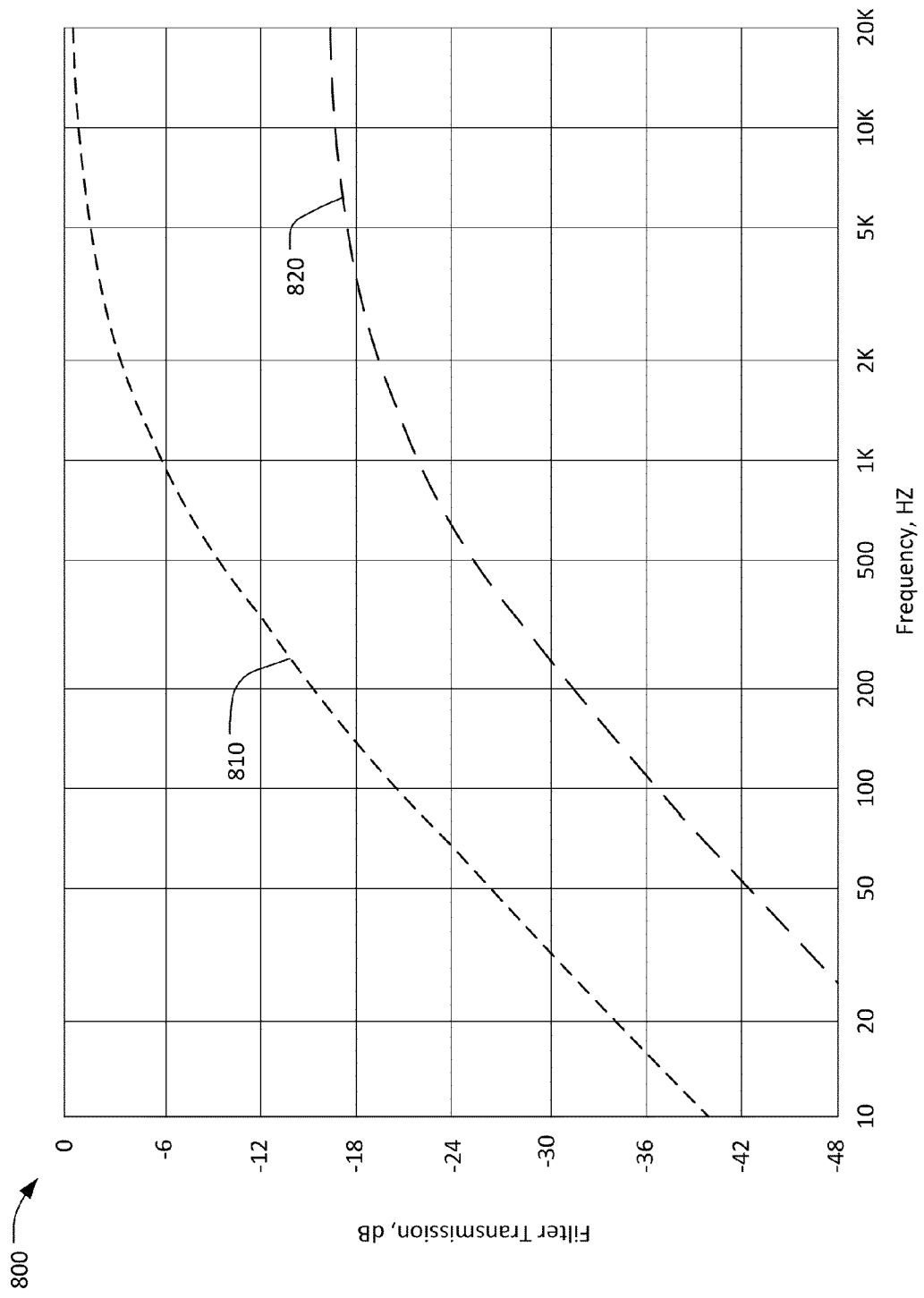
FIG. 8 is a graph of attenuation curves for two low-pass filter elements such as the low-pass filter element shown in FIG. 7.

FIG. 8 is a graph of transmission curves relating to a travel acoustic filter having the general configuration of the passive acoustic filter 700 as shown in FIG. 7. The transmission curves are plotted along an X axis that represents sound frequency measured in hertz (Hz) and a Y axis that represents transmission (inverse of attenuation) of a passive acoustic filter or filter element measured in decibels (dB). Specifically, FIG. 8, includes a curve 810 that represents the transmission of a loss-less high-pass filter (e.g., the high-pass filter shown in FIG. 7 and defined in Table 3) as a function of frequency. FIG. 8 also includes a curve 820 that represents the transmission of a realistic travel acoustic filter including attenuation that occurs in the narrow diameter main branch of the filter A travel acoustic filter can be designed to attenuate low and mid-range frequencies, while allowing high-range frequencies to pass through the filter unchanged or attenuated by a predetermined amount.

Figure 9:
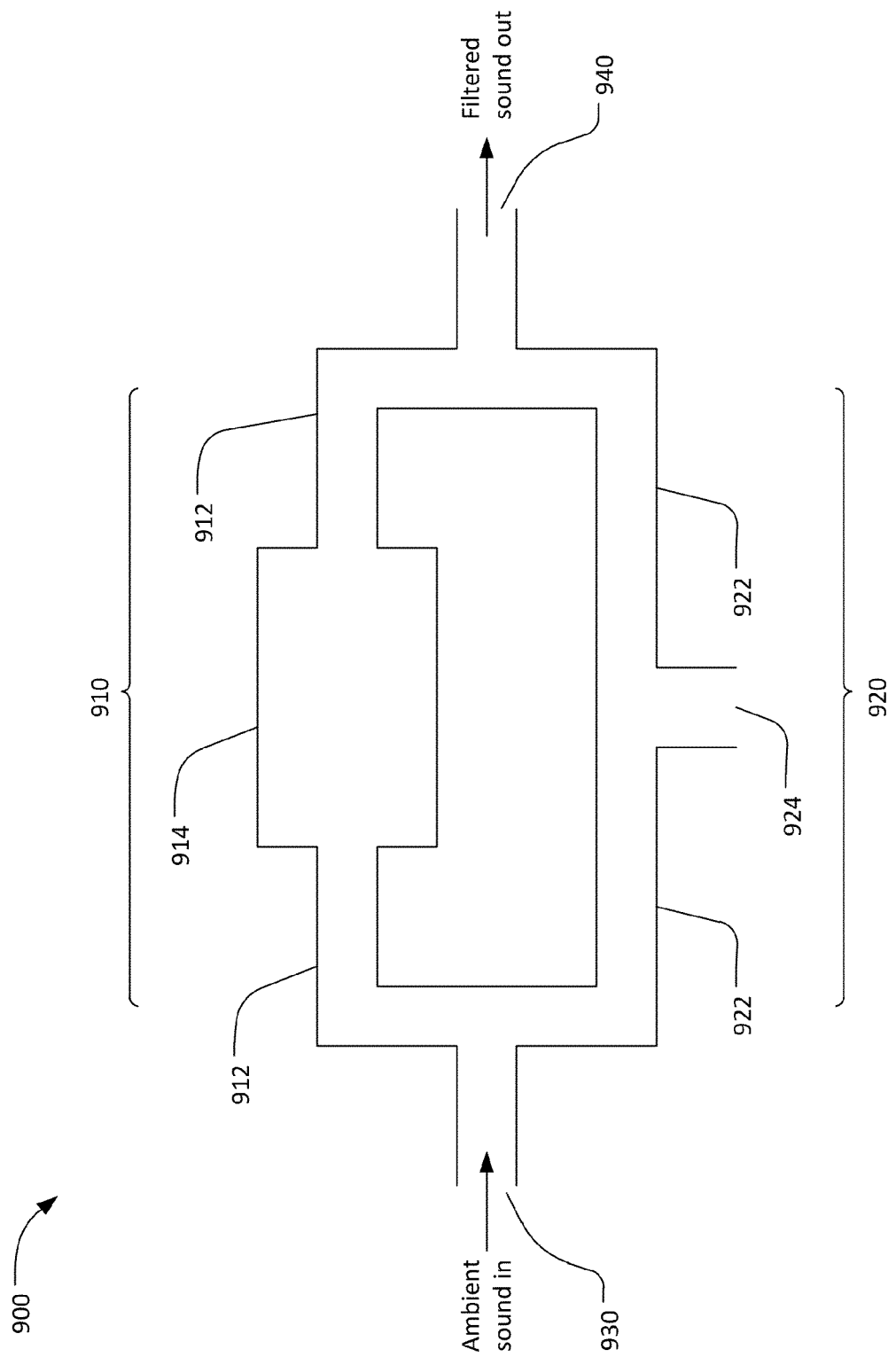
FIG. 9 is a schematic diagram of a passive acoustical filter including a low-pass filter element in parallel with a high-pass filter element.

FIG. 9 is a schematic diagram of a passive acoustical filter 900 that can be used to protect from hearing damage and/or audio disturbance associated with attending a sports event or participating in motor sport activities (e.g., jet skiing, wave running, motorcycling). The passive acoustical filter 900 includes a single stage low-pass filter element 910 and a single stage high-pass filter element 920 in parallel. The configuration of a single stage low-pass filter element and a single stage high-pass filter element in parallel will be referred to herein as a "sports filter". The low-pass filter element 910 includes a main branch 912 and an expansion chamber 914. The high-pass filter element includes a main branch 922 and a side branch 924. In operation, ambient sound can enter the passive acoustical filter 900 at one opening 930, and certain sound frequencies can be filtered as the ambient sound passes through the low-pass filter element 910 and the high-pass filter element 920. The filtered sound can exit the passive acoustical filter 900 at the opposite opening 940.

Exemplary dimensions for the low-pass filter element 910 are set forth in Table 4 below:

TABLE 4

| Exemplary Dimensions for the low-pass filter element 910 | |
|---|---|
| Main branch 912 diameter | 0.8 mm |
| Expansion chamber 914 diameter | 5 mm |
| Expansion chamber 914 length | 12 mm |

The disclosed dimensions can be derived from the equation for the low-pass filter set forth above. Further, these dimensions can be useful for creating a compact sports filter that can be inserted into ear buds, headphones or other apparatuses that fit into or outside an ear, and for achieving an exemplary cutoff frequency for the low-pass filter element of approximately 240 Hz.

Further, a reticulated material having dimensions approximate to the expansion chamber 930 can optionally be placed in the expansion chamber of the low-pass filter 910 to reduce the speed of sound and thus lower the cut-off frequency of the low-pass filter element 910 to approximately 160 Hz.

Exemplary dimensions for the high-pass filter element 920 are set forth in Table 5 below:

TABLE 5

| Exemplary dimensions for the high-pass filter element 920 | |
|---|---|
| Side branch 924 diameter | 0.8 mm |
| Side branch 924 length | 12 mm |
| Main branch 922 diameter | 0.8 mm |

The disclosed dimensions can be derived from the equation for the high-pass filter set forth above. Further, these dimensions can be useful for creating a compact sports filter that can be inserted into earbuds, headphones or other apparatuses that fit into or outside an ear, and for achieving an exemplary cutoff frequency for the high-pass filter element of approximately 4.5 kHz.

The dimensions described above for the low-pass filter element 910 and the high-pass filter element 920 of the passive acoustical filter 900 are non-limiting examples, and other dimensions that can achieve similar hearing protection for sports events and motor activities may also be used. Additionally, the dimensions described above can be tailored for indoor versus outdoor sports stadium use. Because indoor stadiums generate greater midrange sound frequencies than outdoor stadiums, an indoor sports acoustical filter may be designed to attenuate more midrange frequencies (e.g., the midrange sound frequencies generated by peoples' voices) relative to the bass and treble sounds (e.g., from feet stomping, sound systems and fireworks). For example, the cut-off frequency of the low-pass filter element may be 50 to 3000 Hz, and the cutoff frequency of the high pass filter element may be 1,000 to 20,000 Hz.

Figure 10:
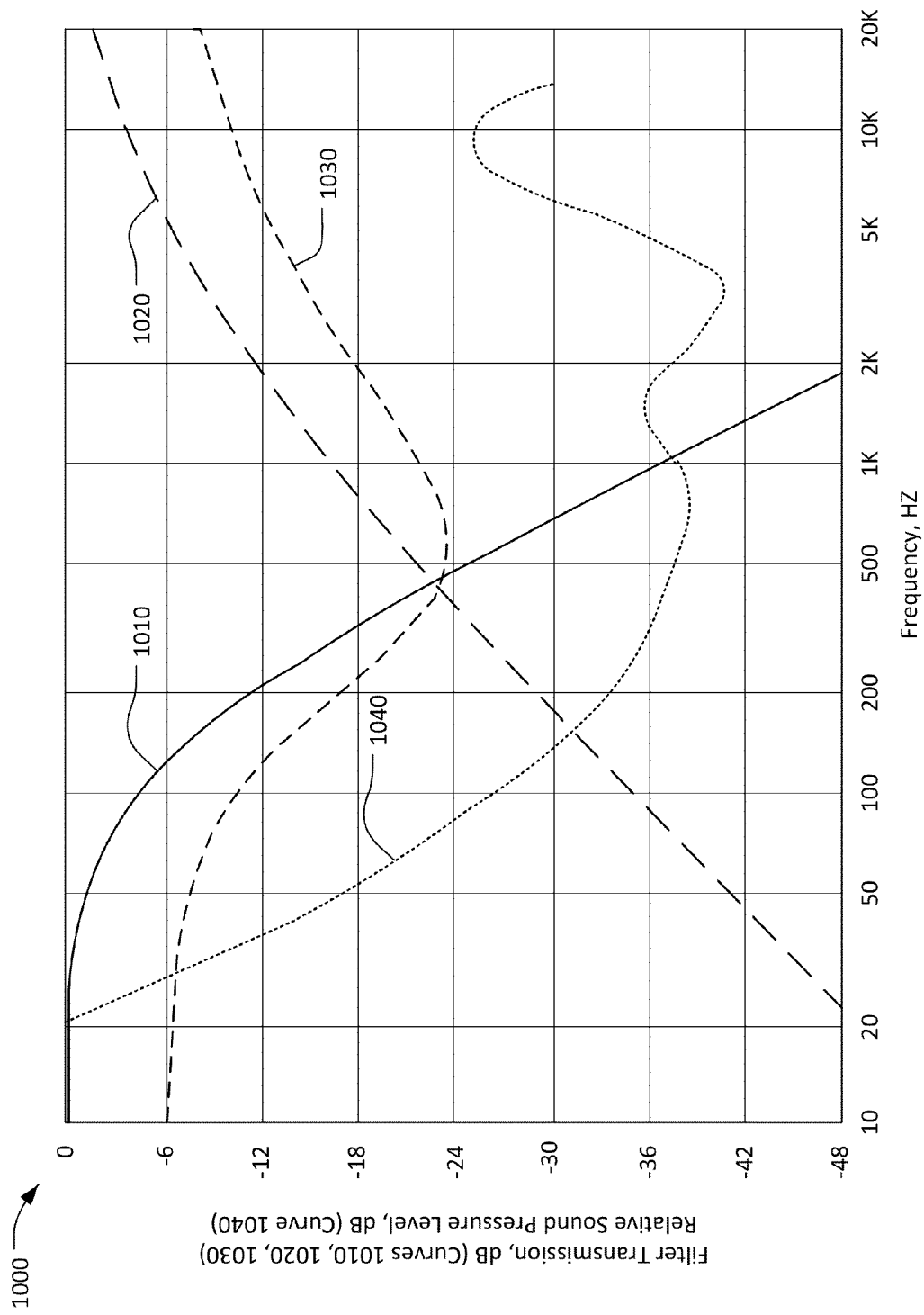
FIG. 10 is a graph of attenuation curves relating to the passive acoustical filter of FIG. 9.

FIG. 10 is a graph of transmission curves relating to a sports acoustic filter having the general configuration of the passive acoustic filter 900 as shown in FIG. 9. Like FIG. 6 and FIG. 8, the transmission curves are plotted along an X axis that represents sound frequency measured in hertz (Hz) and a Y axis that represents transmission (inverse of attenuation) of a passive acoustic filter or filter element measured in decibels (dB). The curve 1010 represents the transmission of a lossless low-pass filter element having the dimensions given in Table 4. The curve 1020 represents the transmission of a loss-less high-pass filter element having the dimensions given in Table 5. The curve 1030 represents the combined transmission of the double stage low-pass filter in parallel with the single stage high-pass filter, including attenuation that occurs in the narrow diameter main branches of the low-pass and high-pass filter elements. The curve 1040 is the 80 Phon loudness level from FIG. 1, normalized to 0 dB at 20 Hz. The curve 1040 represents the sound pressure level required to produce apparently equal loudness as a function of frequency. As illustrated in FIG. 10, the performance of the sports acoustic filter (as summarized by the transmission curve 1030) compliments the 80 Phon equal loudness curve 1040, in that the filter provides highest attenuation (lowest transmission) at frequencies where the human ear is most sensitive, and lowest attenuation (highest transmission) for low and high frequencies where the ear is less sensitive.

Figure 11:
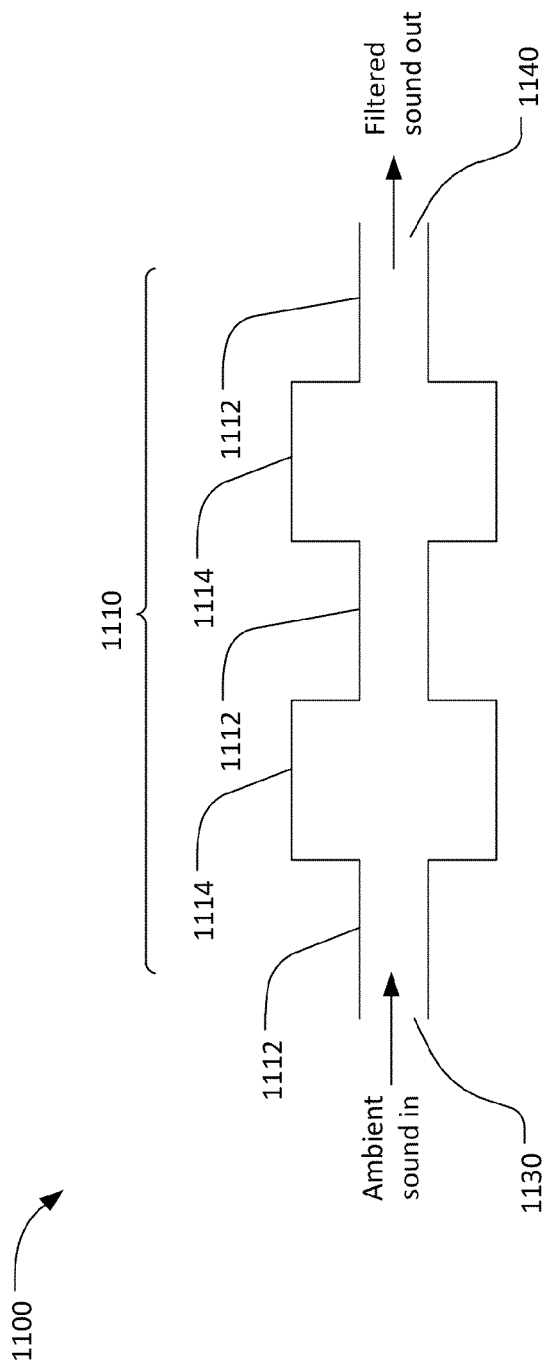
FIG. 11 is a schematic diagram of a passive acoustical filter including two low-pass filter elements in series.

FIG. 11 is a schematic diagram of a passive acoustical filter 1100 that can be used within earbuds, headphones or other apparatuses to protect a human's auditory system from auditory disturbance during sleep. Acoustical filter 1100 includes a double stage low-pass filter 1110 including two low-pass filter elements in series. A filter configuration consisting of two low-pass filter elements in series will be referred to herein as a "sleep filter". The low pass filter elements have respective expansion chambers 1114 connected by a main branch 1112. In operation, ambient sound can enter the passive acoustical filter 1100 at one opening 1130, and certain sound frequencies can be filtered as the ambient sound passes through the main branch 11112 and two expansion chambers 1114. The filtered sound can exit the passive acoustical filter 1100 at the opposite opening 1140.

Exemplary dimensions for the sleep filter, in accordance with an embodiment of the disclosed subject matter, are set forth in the table below:

TABLE 6

Exemplary Dimensions for the passive acoustical filter 1100

| | |
|---|---|
| Main branch 1112 diameter | 0.5 mm |
| Expansion chamber 1114 diameter | 4 mm |
| Expansion chamber 1114 length | 13 mm |

These dimensions can be derived from the equation for the low-pass filter set forth above. Further, these dimensions can be useful for creating a compact filter that can be inserted into earbuds, headphones or other apparatuses that fit into or outside an ear, and for achieving an exemplary cutoff frequency for the low-pass filter of approximately 130 Hz.

Further, reticulated material (e.g., foam) having dimensions approximate to the expansion chambers 1114 can optionally be inserted into the expansion chambers 1120 of the double stage low-pass filter 1100 to reduce the speed of sound and lower the cutoff frequency to 90 Hz.

The dimensions described above for the double stage low-pass filter of the sleep filter are non-limiting examples, and other dimensions that can achieve similar hearing protection from sleep disturbances may also be used. For example, the cut-off frequency of each low-pass filter element may be 50 to 3000 Hz.

Figure 12:
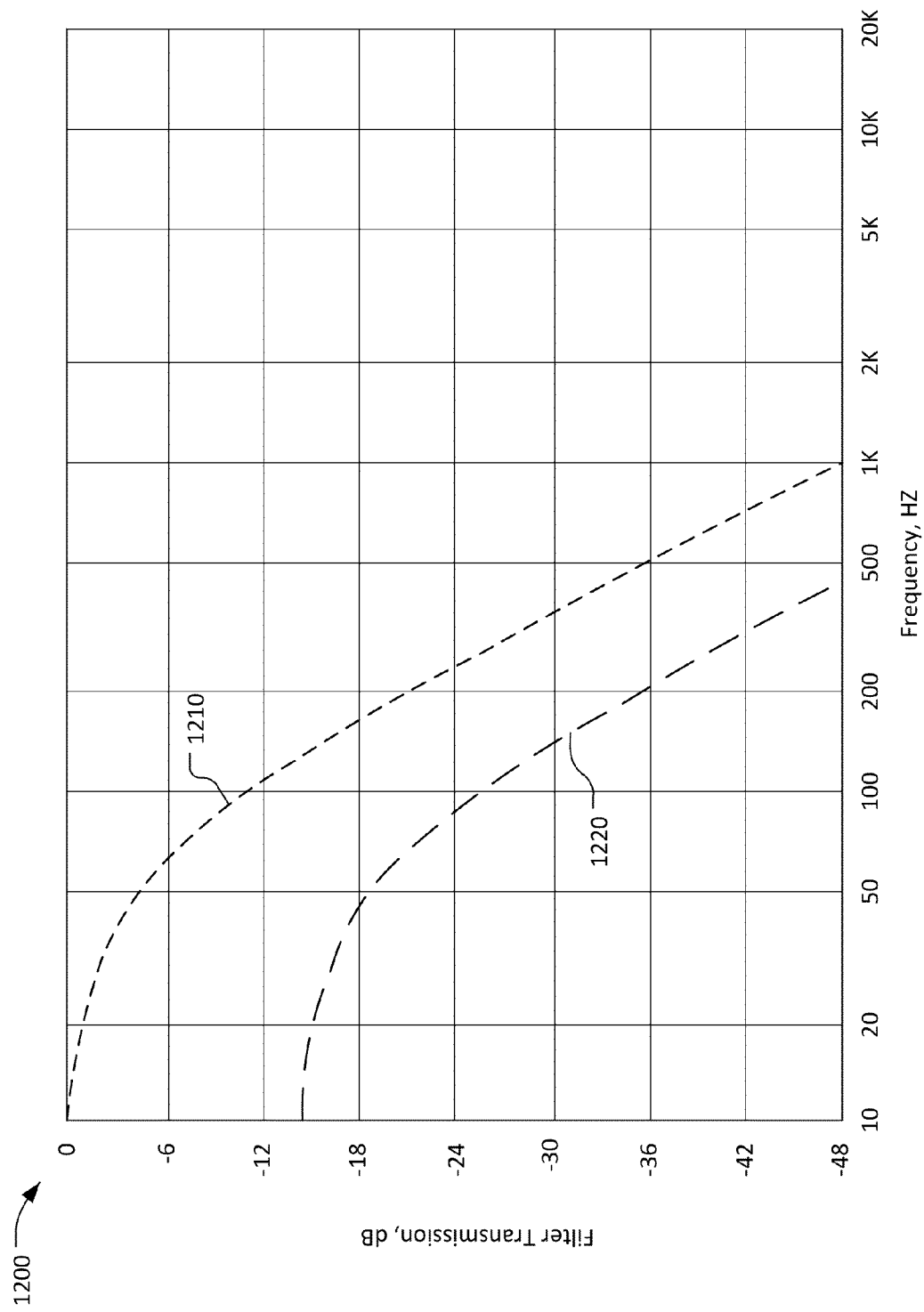
FIG. 12 is a graph of attenuation curves relating to the passive acoustical filter of FIG. 11.

FIG. 12 is a graph of transmission curves relating to a sleep acoustic filter having the general configuration of the passive acoustic filter 1100 as shown in FIG. 11. The transmission curves are plotted along an X axis that represents sound frequency measured in hertz (Hz) and a Y axis that represents transmission (inverse of attenuation) of a passive acoustic filter or filter element measured in decibels (dB). Specifically, FIG. 12 includes a curve 1210 that represents the transmission of an exemplary loss-less double-stage low-pass filter (e.g., the double stage low-pass filter shown in FIG. 11 and defined in Table 6) as a function of frequency. FIG. 12 also includes a curve 1220 that represents the transmission of the exemplary double-stage low-pass filter including attenuation that occurs in the narrow main branch of the filter. The use of the reticulated material may be used to lower the cut-off frequency of the double-stage low-pass filter. A sleep acoustical filter can be designed to attenuate mid- and high-range frequencies, while allowing low-range frequencies to pass through the filter unchanged or with a predetermined attenuation.

Other passive acoustical filters may include a band-reject filter element to attenuate frequencies at a specific frequency range. The dimensions of the band-reject filter element can be tailored to filter out sound at a targeted frequency range on the sound frequency spectrum. For example, a band-reject filter element, similar to the example shown in FIG. 4, can be used to filter our sound frequencies associated with a consistent whine or hum (e.g., power generation plant), while allowing other frequencies to pass through.

Other passive acoustical filters may include a band-pass filter element can be used to allow only a specific range of sound frequencies to pass through unchanged, while attenuating sounds at all other frequencies. A band-pass filter element may be realized, for example, by placing a low-pass filter element and a high-pass filter element in series, with the cutoff frequency of the high-pass filter element set lower than the cutoff frequency of the low-pass filter element.

Passive acoustical filters, such as those described above, may be disposed within a housing that can be substantially contained within the ear (e.g., in the ear canal, concha, and/or pinna. Passive acoustical filters, such as those described above, may be disposed outside the ear in a headphone apparatus or any other apparatus that allows ambient sound to travel through an acoustical filter.

FIG. 13A is a graphical image of components of an exemplary musical acoustical filter 1300. The musical acoustic filter 1300 includes housing 1310 made of a plastic or metal material, a center divider 1320, two reticulated inserts 1330, and first and second end caps 1340, 1350. In this example, the housing 1310 is a cylindrical tube. The housing 1310 may have a cross-sectional shape other than cylindrical, such as square or hexagonal. The reticulated inserts 1330 may include an adhesive backing for attaching to the center divider 1320. The end caps 1340, 1350 incorporate apertures for the input and output of the music acoustical filter 1300 and channels that connect the other elements of the music acoustical filter 1300. In this context, the term "channels" means any passage through which acoustic waves may pass. Channels may commonly be cylindrical passages or tubes. As shown in the cross-sectional schematic view of FIG. 13B, the center divider 1320 together with the walls of the outer tube 1310 form two expansion chambers 1360 that are substantially filled by the reticulated inserts 1330. Additionally, first and second longitudinal channels 1322, 1324 run through the length the center divider 1320.

Figure 14:
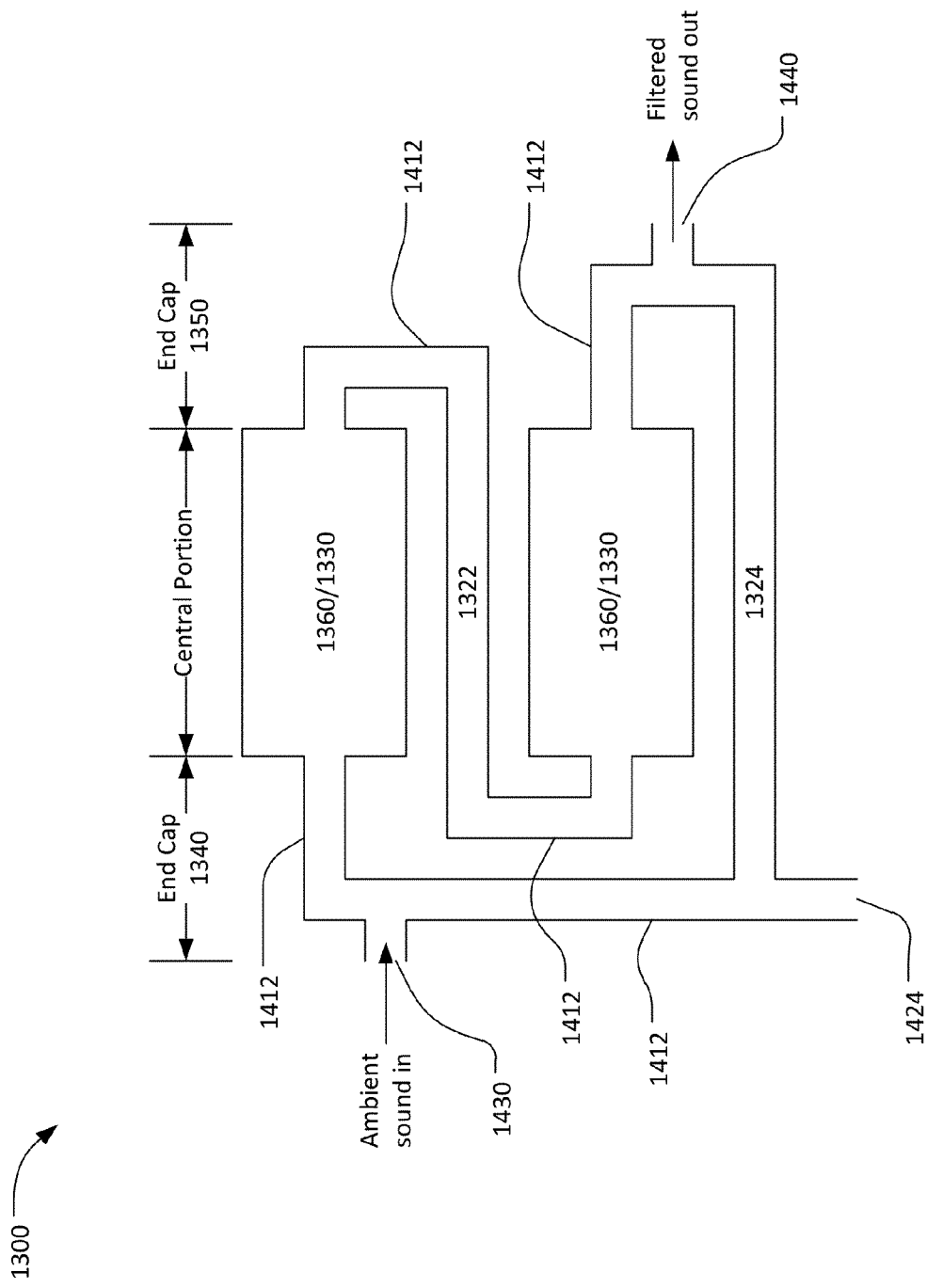
FIG. 14 is a schematic diagram of the music acoustical filter assembled form the components shown in FIG. 13A.
Figure 15:
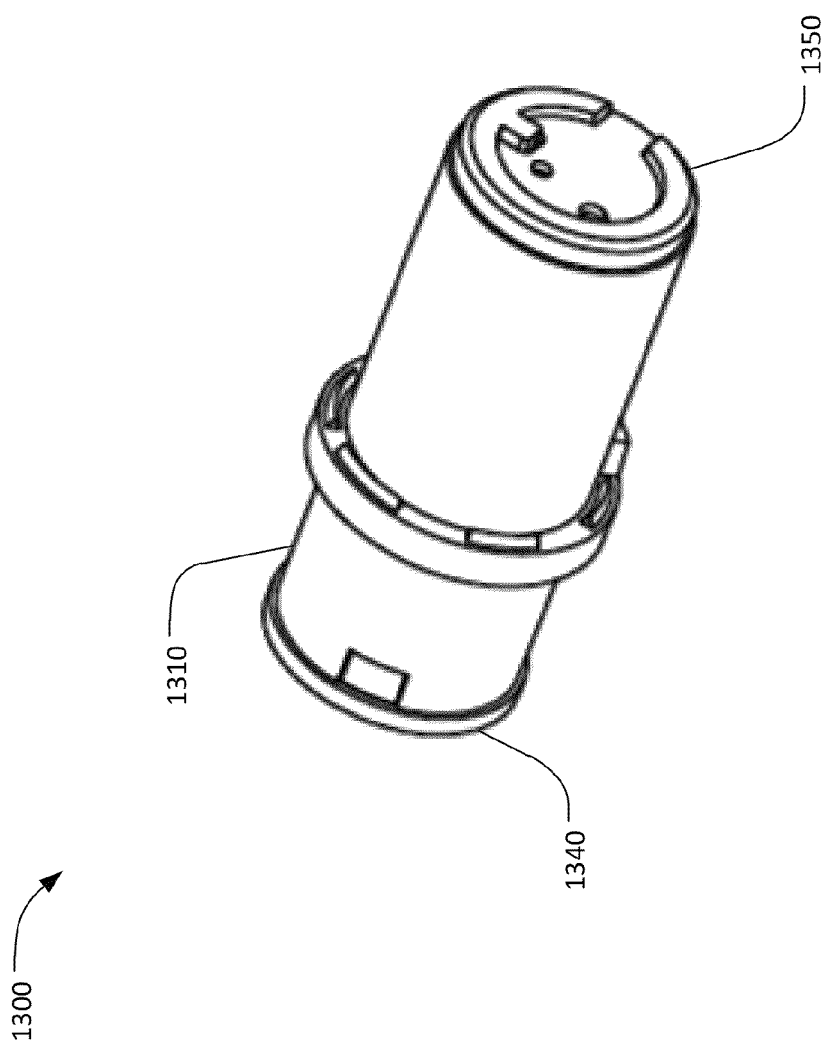
FIG. 15 is a graphical image of the passive acoustical filter assembled from the components shown in FIG. 13A.

FIG. 14 is a schematic diagram of the music acoustical filter 1300. The central portion of the device (comprising the outer tube 1310, center divider 1320, and reticulated inserts 1330, as shown in FIG. 13A) includes two expansions chambers 1360 that are substantially filled by reticulated inserts 1330. The two expansion chambers are connected in series by the first longitudinal channel 1322 (running the length of the center divider 1320) and channels 1412 (formed in the end caps 1340, 1350) to form a two-stage low pass filter. The second longitudinal channel 1324 (running the length of the center divider 1320) forms the main branch of a high-pass filter element, which is connected in parallel to the two-stage low-pass filter element by additional channels 1412 in the end caps 1340, 1350. One of the end caps (end cap 1340 as shown in FIG. 14) includes a side branch 1424 of the high-pass filter element. Ambient sound can enter the music acoustical filter 1300 through an aperture 1430 in end cap 1340 and certain sound frequencies can be filtered as the ambient sound passes through the high-pass filter element and the dual-stage low-pass filter element. The resulting filtered sound can exit the music acoustical filter 1300 through an aperture 1440 in end cap 1350. The filtered sound exiting at 1440 may be approximately the sum of the sound passing through the double-stage low-pass filter element and the sound passing through the high-pass filter element. The dimensions of the music acoustical filter 1300 may be selected to provide the desired filter function, as previously discussed with respect to the music acoustical filter 500 of FIG. 5. FIG. 15 is a graphical image of the exemplary music acoustical filter 1300 assembled from the components shown in FIG. 13A. The outer tube 1310 and end caps 1340, 1350 are visible.

Figure 16:
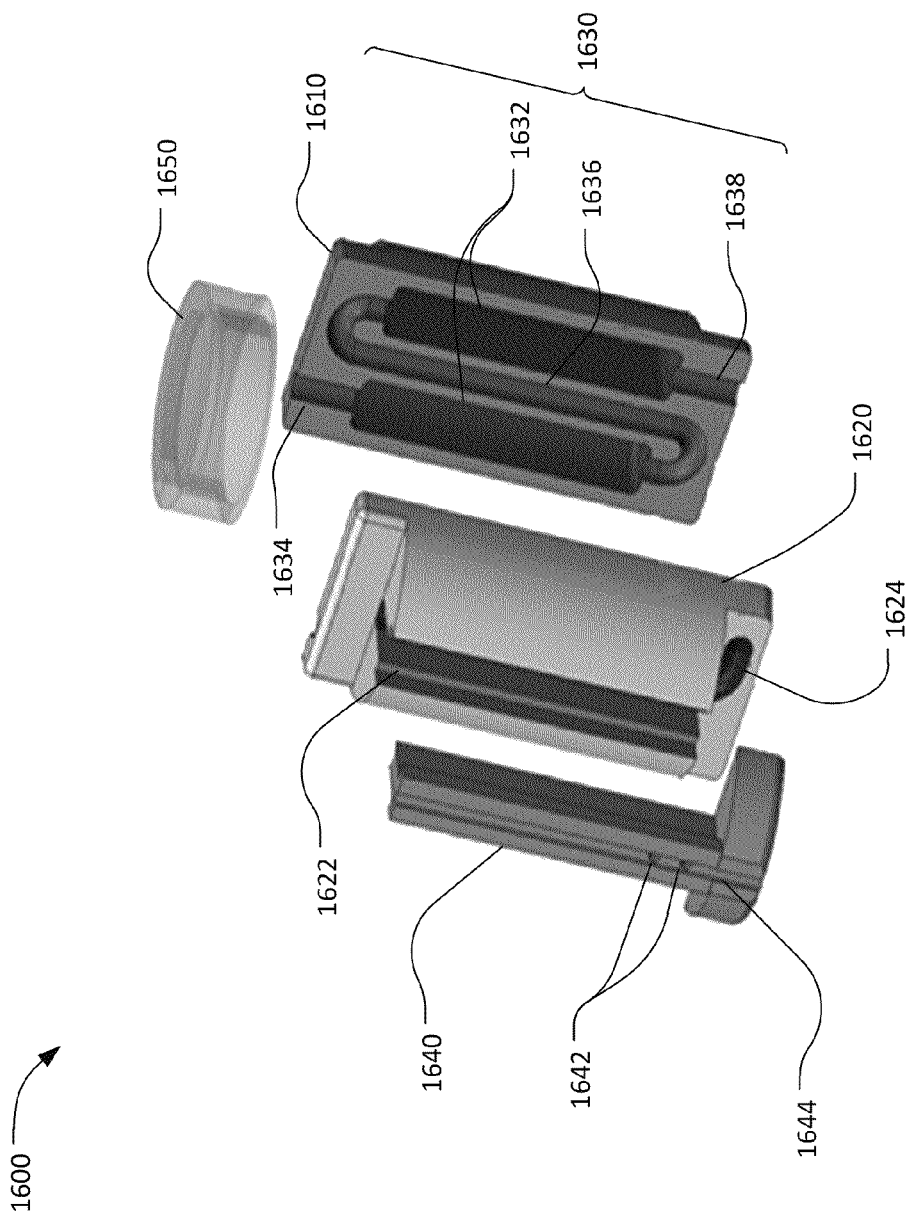
FIG. 16 is an exploded graphical image of another music acoustical filter.

FIG. 16 shows an exploded view of another exemplary music acoustical filter 1600. The exploded music acoustical filter 1600 includes a double stage low-pass filter formed by a first body piece 1610 and a second body piece 1620. The first and second body pieces 1610, 1620 may formed from a plastic material such as polycarbonate. Each of the first body piece 1610 and the second body piece 1620 includes a symmetric half of a double-stage low-pass filter element 1630 in the shape of an "S." First body piece 1610 includes half-cylindrical recesses forming two expansion chambers 1632 and connecting channels 1634, 1636, 1638. Second body piece 1620 includes mirror images recesses (not visible). When assembled, the first body piece 1610 and the second body piece 1620 collectively form two cylindrical expansion chambers connected in series by cylindrical main channels.

The second body piece 1620 also includes a cavity 1622 for placement of an insert 1640 which may be formed from polycarbonate or another plastic. When the insert 1640 is placed into the cavity 1622, an interstitial space between the insert 1640 and the second body piece 1620 forms a main branch of a high-pass filter element. A side branch of the high-pass filter element is formed by the two holes 1642. Two holes are used in this example to provide sufficient cross-sectional area for the side branch. A passage 1624 in the body piece 1620 may couple the high-pass filter element to the channel 1638. A groove 1644 in the insert 1640 provides an outlet to the ambient for the side branch of the high-pass filter element.

An end cap 1650 may fit over the end portions of first and second body pieces 1610 and 1620 to hold the pieces in alignment. The end cap may optionally include a scrim cloth designed to protect the filter from ear surface contaminants.

Figure 17:
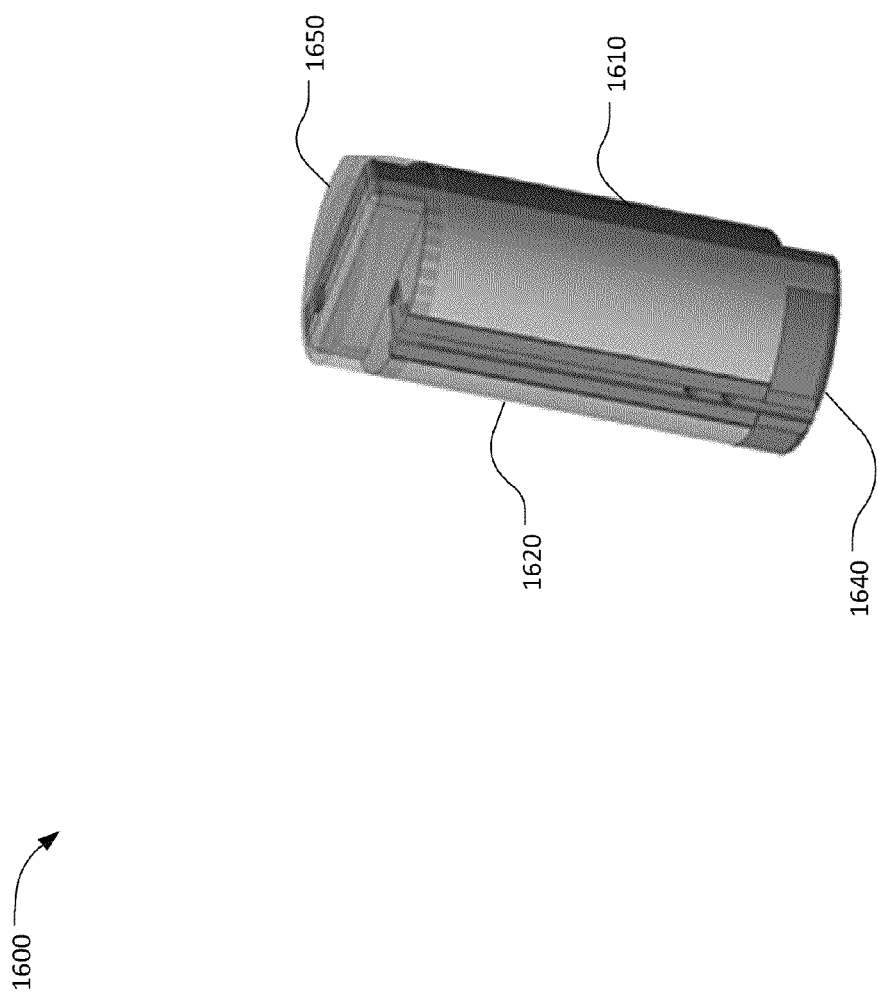
FIG. 17 is a graphical image of the music acoustical filter assembled from the components shown in FIG. 16.

FIG. 17 shows the exemplary music filter 1600 assembled from the components shown in FIG. 16. FIG. 17 shows the first body piece 1610, the second body piece 1620, the inset 1640, and the end cap 1650.

Figure 18:
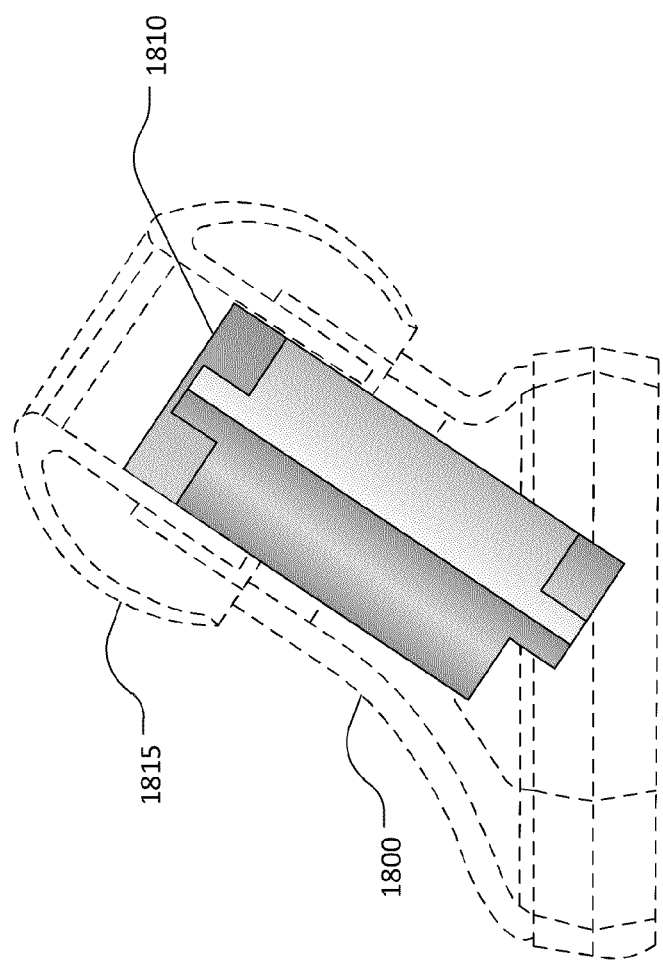
FIG. 18 is a graphical image of an exemplary music acoustical filter within an earbud.

FIG. 18 shows a transparent view of an exemplary earbud 1800 containing an acoustical filter 1810, which may be, for example, the music acoustic filter 1600 (as shown in FIG. 17) or the music acoustical filter 1300 (as shown in FIG. 15). The music acoustical filter 1810 is shown inserted into the neck of the exemplary earbud 1800. An outer removable cap 1815 may be positioned on top of the filter and can be inserted into the ear. The exemplary earbud 1800 may be, for example, the earbud described in Design patent application 29/485,359.

Passive acoustical filters as described above can be designed to be interchangeable, so they can each fit into the same sized earbud, headphone or other apparatus. Designing various passive acoustic filters for interchangeability can allow for the different types of acoustic filters to be swapped in and out of the earbud, headphone or other apparatus, in order to match the type of auditory protection desired for different environments and/or activities.

CLOSING COMMENTS

Throughout this description, the embodiments and examples shown should be considered as exemplars, rather than limitations on the apparatus and procedures disclosed or claimed. Although many of the examples presented herein involve specific combinations of elements, it should be understood that those elements may be combined in other ways to accomplish the same objectives. Elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:
1. A passive acoustical filter to be coupled between an ambient and an ear of a listener, comprising:
   a high-pass filter element; and
   a series combination of two low-pass filter elements in parallel with the high-pass filter element.
2. The passive acoustical filter of claim 1, further comprising:
   an earbud enclosing the high-pass filter element and the series combination of two low-pass filter elements.
3. The passive acoustical filter of claim 1, wherein
   each of the two low-pass filter elements has a cutoff frequency of 160 Hz to 240 Hz, and
   the high-pass filter element has a cutoff frequency of 14,600 Hz to 21,800 Hz.
4. The passive acoustical filter of claim 1, further comprising:
   a housing having a length and first and second open ends;
   a center divider running along the length of the housing to form two expansion chambers;
   a first end cap closing the first end of the housing; and
   a second end cap closing the second end of the housing,
     wherein the center divider, the first end cap, and the second end cap collectively include channels to connect the two expansion chambers to form the series combination of two low-pass filter elements.

5. The passive acoustical filter of claim 4, further comprising:
   two reticulated inserts that substantially fill the two expansion chambers.

6. The passive acoustical filter of claim 4, wherein
   the center divider includes first and second longitudinal channels running parallel to the length of the housing, the first longitudinal channel being part of a connection between the two expansion chambers, and the second longitudinal channel being part of a main branch of the high-pass filter element.

7. The passive acoustical filter of claim 6, wherein the first end cap comprises:
   a first aperture open to a environment; and
   channels to connect the first aperture to the first expansion chamber, to connect the first aperture to the second longitudinal channel, and to connect the second expansion chamber to the first longitudinal channel.

8. The passive acoustical filter of claim 7, wherein the second end cap comprises:
   a second aperture open to a environment;
   a high-pass filter side branch connected to the second longitudinal channel; and
   channels to connect the second aperture to the second expansion chamber, to connect the second aperture to the second longitudinal channel, and to connect the first expansion chamber to the first longitudinal channel.

9. The passive acoustical filter of claim 4, wherein the housing is a cylindrical tube.

10. The passive acoustical filter of claim 1, further comprising:
    a first body piece having a first face;
    a second body piece having a cavity and a second face in contact with the first face; and
    an insert disposed to partially fill the cavity, wherein
    the first face and the second face have recesses forming the series combination of two low-pass filter elements, and
    an interstitial space between the insert and the second body piece forms a main branch of the high-pass filter element and one or more holes in the insert form a side branch of the high-pass filter element.

11. The passive acoustical filter of claim 10, wherein
    the recesses in the first face include two half-cylindrical expansion chamber portions and connecting channel portions disposed in an "S" pattern; and
    the recesses in the second face are a mirror image of the recesses in the first face.

12. The passive acoustical filter of claim 10, further comprising:
    an end cap to hold the first body piece and the second body piece in alignment.

* * * * *